United States Patent
Karakosta et al.

(10) Patent No.: US 11,322,238 B2
(45) Date of Patent: May 3, 2022

(54) DEFAULT DATA SET DISTRIBUTION FOR MEDICAL DEVICES

(71) Applicant: Fenwal, Inc., Lake Zurich, IL (US)

(72) Inventors: Thomas Karakosta, Chicago, IL (US); Witold Moskal, Park Ridge, IL (US)

(73) Assignee: Fenwal, Inc., Lake Zurich, IL (US)

( * ) Notice: Subject to any disclaimer, the term of this patent is extended or adjusted under 35 U.S.C. 154(b) by 237 days.

(21) Appl. No.: 15/452,556

(22) Filed: Mar. 7, 2017

(65) Prior Publication Data
US 2017/0262590 A1    Sep. 14, 2017

Related U.S. Application Data

(60) Provisional application No. 62/307,985, filed on Mar. 14, 2016.

(51) Int. Cl.
| | |
|---|---|
| *G16H 20/17* | (2018.01) |
| *G16H 40/63* | (2018.01) |
| *G16H 40/40* | (2018.01) |
| *G16H 40/67* | (2018.01) |
| *G16H 70/40* | (2018.01) |

(52) U.S. Cl.
CPC ............ *G16H 20/17* (2018.01); *G16H 40/40* (2018.01); *G16H 40/63* (2018.01); *G16H 40/67* (2018.01); *G16H 70/40* (2018.01)

(58) Field of Classification Search
CPC ........ G16H 20/10; G16H 20/17; G16H 70/40; G16H 40/40–67; G06F 8/71
See application file for complete search history.

(56) References Cited

U.S. PATENT DOCUMENTS

| | | | |
|---|---|---|---|
| 9,311,066 B1 * | 4/2016 | Garman | G06F 8/60 |
| 2003/0140929 A1 * | 7/2003 | Wilkes | G06F 19/3468 128/898 |
| 2006/0026205 A1 * | 2/2006 | Butterfield | G16H 40/63 |
| 2007/0106980 A1 * | 5/2007 | Felts | G06F 9/44536 717/124 |

(Continued)

OTHER PUBLICATIONS

J Moldenhauer, SCCM 2012—Deploying Updates, Dec. 17, 2013, Jim Moldenhauer's Tech Blog (Year: 2013).*

(Continued)

*Primary Examiner* — Christopher L Gilligan
*Assistant Examiner* — Karen A Hranek
(74) *Attorney, Agent, or Firm* — Cook Alex Ltd.

(57) ABSTRACT

A computer-implemented medical device management method for distributing data sets to a plurality of medical devices in child locations of a parent health organization includes providing a first data set, receiving a first user input to distribute the first data set, distributing the first data set to medical devices located in child locations within the parent organization, and facilitating operation of the medical devices according to the first data set. The method also includes providing a second data set different from the first, receiving, after the first user input, a second user input to distribute the second data set to target medical devices, commencing distribution of the second data set prior to completing distribution of the first data set, and stopping distribution of the first data set for all medical devices that have not yet received the first data set and that are target medical devices.

19 Claims, 17 Drawing Sheets

(56) References Cited

U.S. PATENT DOCUMENTS

| | | | |
|---|---|---|---|
| 2007/0213598 A1* | 9/2007 | Howard | A61M 5/142 600/300 |
| 2007/0271115 A1* | 11/2007 | Baldus | G16Z 99/00 705/2 |
| 2008/0154177 A1* | 6/2008 | Moubayed | G06F 19/3468 604/19 |
| 2009/0157430 A1* | 6/2009 | Rule | A61B 5/0002 705/3 |
| 2010/0049542 A1 | 2/2010 | Benjamin et al. | |
| 2010/0274098 A1* | 10/2010 | Belford | G16H 40/63 600/300 |
| 2013/0104120 A1* | 4/2013 | Arrizza | G06F 8/65 717/173 |
| 2013/0110538 A1 | 5/2013 | Jordan | |
| 2014/0180711 A1* | 6/2014 | Kamen | G16H 20/10 705/2 |
| 2014/0215028 A1* | 7/2014 | Donner | H04L 41/16 709/220 |
| 2015/0370973 A1 | 12/2015 | Jones | |
| 2015/0371004 A1* | 12/2015 | Jones | G06F 19/326 705/2 |
| 2016/0034655 A1* | 2/2016 | Gray | A61M 5/142 713/1 |
| 2016/0092196 A1* | 3/2016 | Kuchibhotla | G06F 8/65 717/170 |
| 2016/0339167 A1* | 11/2016 | Ledford | G06F 19/326 |
| 2016/0350513 A1* | 12/2016 | Jacobson | G06F 19/3468 |
| 2017/0147761 A1 | 5/2017 | Moskal et al. | |
| 2017/0242969 A1* | 8/2017 | Baudet | A61B 5/7435 |

OTHER PUBLICATIONS

European Patent Office, European Search Report, European Patent Application No. 17158671.2, dated May 19, 2017; 15 pages.

* cited by examiner

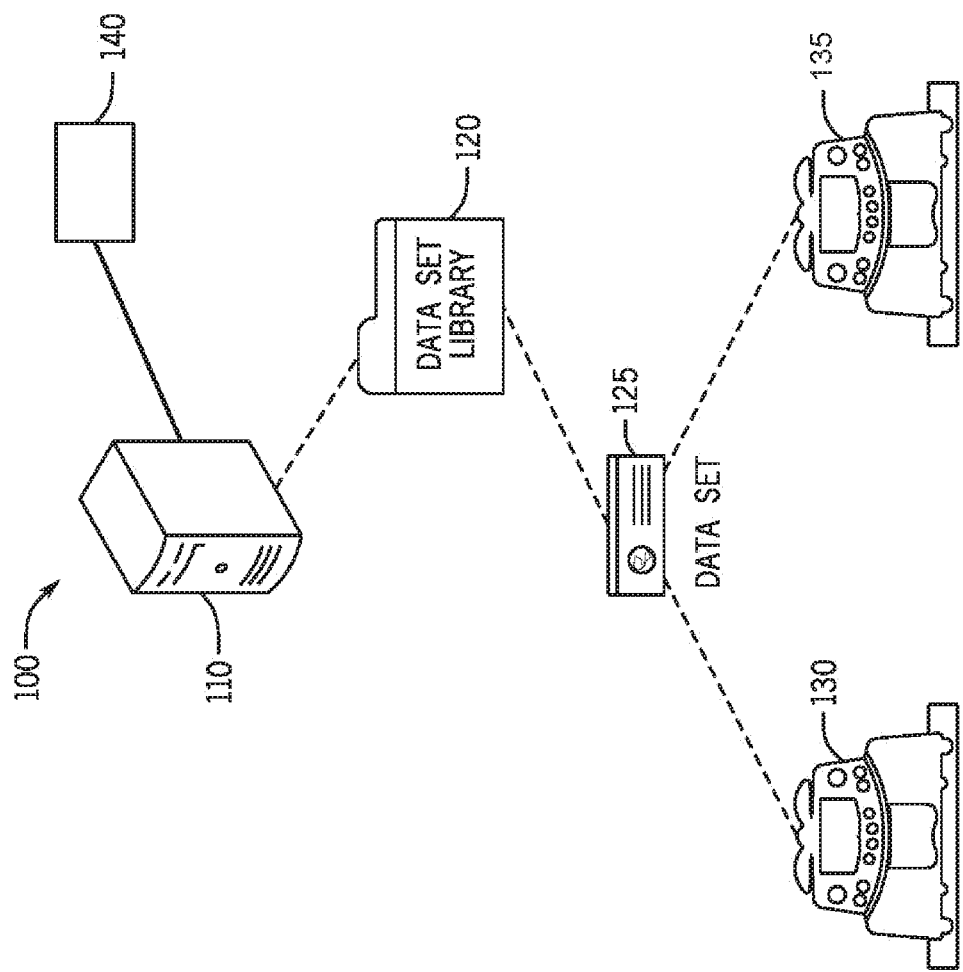

NOT FOR HUMAN USE

| CONFIGURATION | HOSPITALS | | | | 57 — CREATE HOSPITAL |
|---|---|---|---|---|---|
| CONFIGURATION | ORGANIZATION | HOSPITALS | ROLES | LANGUAGES | |
| NAME | ~ ADDRESS LINE 1 | | USER GROUP NAME | | |
| GERI HOSPITAL A1 — 41a | | | | | |
| GERI HOSPITAL B1 — 41b | | | | | |
| GERI HOSPITAL C1 — 41c | | | | | |

| DATA SETS | DOUG 2015-11-05-000 | CONFIRM POLICY BY HOSPITAL | NOT FOR HUMAN USE | 56 — [CREATE] |
|---|---|---|

| | HOSPITAL | PUMPS TOTAL |
|---|---|---|
| + ☐ | GERI_HOSPITAL A1 — 41a | 1 [VIEW PUMPS] |
| + ☐ | GERI_HOSPITAL B1 — 41b | 1 [VIEW PUMPS] |
| + ☒ 55 | GERI_HOSPITAL C1 ↙ 41c | 1 [VIEW PUMPS] |

NOT FOR HUMAN USE

| CONFIGURATION | HOSPITALS | | | CREATE HOSPITAL |
|---|---|---|---|---|
| ORGANIZATION | HOSPITALS | ROLES | LANGAUGES | |

| NAME | ~ ADDRESS LINE 1 | USER GROUP NAME | | |
|---|---|---|---|---|
| GERI_HOSPITAL A1 | | | | |
| GERI_HOSPITAL B1 | | | | |
| GERI_HOSPITAL C1 | | | | |
| GERI_HOSPITAL D1 ← 41d | | | | |

DEFAULT DATA SET DISTRIBUTION FOR MEDICAL DEVICES

CROSS-REFERENCE TO RELATED APPLICATIONS

This application claims the benefit of U.S. Provisional Patent App. No. 62/307,985 filed Mar. 14, 2016, which is expressly incorporated herein by reference in its entirety.

FIELD OF THE DISCLOSURE

The present disclosure is directed to data distribution to medical devices. More specifically, the present disclosure relates to methods, systems, and apparatus to facilitate default data set distribution for medical devices.

BACKGROUND

Infusion pumps are used in the field of medicine to administer drugs to patients often over an extended time period. The time period of infusion may be longer than can be managed easily by direct injection. Sophistication in drug delivery has increased as availability of drugs, therapeutic techniques, and technological capabilities have improved. Achieving this sophistication in drug delivery capability and maintaining ease of use have become more important for infusion pump manufacturers.

Infusion pumps are used to administer drugs and other medicaments often in a clinical setting. An infusion pump may provide a controlled amount of the medicament over time to the patient. The amount may be administered pursuant to parameters entered, for example, by a clinician into the pump using a pump user interface.

To avoid errors in drug administration, some infusion pumps may hold a library of drug names and associated parameters, e.g., rate of infusion, frequency of infusion, etc. The drug library may be created and/or updated by a health care professional and/or health center employee. In some cases, overriding or reprogramming of parameters programmed into the drug library may be desired.

SUMMARY

According to an exemplary embodiment, the present disclosure is directed to a computer-implemented medical device management method for distributing instructions to a plurality of medical devices, said method comprising providing via a drug library a first data set to be distributed to a parent organization having at least one child location, wherein the at least one child location collectively includes at least one target medical device identified by the first data set. The method also comprises receiving a first user input via a user interface to distribute the first data set to the parent organization. The method also comprises distributing the first data set to the at least one target medical device located in the at least one child location within the parent organization, and facilitating operation of the at least one target medical device according to the first data set.

According to an exemplary embodiment, the present disclosure is directed to a server computer configured to distribute instructions to a plurality of medical devices. The server computer comprises a network interface circuit configured to provide communications over a network, and a processing circuit. The processing circuit is configured to provide via a drug library a first data set to be distributed to a parent organization having at least one child location, wherein the at least one child location collectively includes at least one target medical device identified by the first data set. The processing circuit is also configured to distribute the first data set to the at least one target medical device located in the at least one child location within the parent organization. The processing circuit is also configured to facilitate operation of the at least one target medical device according to the first data set and provide a second data set to be distributed to the at least one child location, wherein the second data set is provided later in time than the first data set. The processing circuit is also configured to distribute the second data set to the at least one target medical device located within the at least one child location, wherein a medical device identified by both the first data set and the second data set is configured to adopt the second data set.

According to an exemplary embodiment, the present disclosure is directed to a computer-implemented medical device management system comprising a data management system comprising analog and/or digital circuit components comprising discrete circuit elements and/or programmed integrated circuits. The medical device management system also comprises a medical device comprising a network interface circuit configured to provide communications over one or more networks with another medical device and/or with the data management system. The medical device management system also comprises a drug library configured to provide a default data set to be distributed by the data management system to a parent organization having at least one child location, wherein the at least one child location collectively includes at least one target medical device identified by the first data set. The data management system is configured to receive a first user input via a user interface to distribute the first data set to the parent organization, to distribute the first data set to the at least one target medical device located in the at least one child location within the parent organization, and to facilitate operation of the at least one target medical device according to the first data set. The data management system is configured to provide a second data set provided by the drug library to be distributed to a child location when it receives a second user input to distribute the second data set to the child location, and is configured to then distribute the second data set to at least one target medical device located within the child location, including target medical devices identified by both the first data set and the second data set.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

FIG. 1 is a schematic diagram of a medical device management system, according to an exemplary embodiment;

FIGS. 4A-4E are illustrations of content on a user interface showing the steps performed by a user to set a distribution policy at a parent location level, according to an exemplary embodiment;

FIGS. 5A-5D are illustrations of content on a user interface showing steps performed by a user to set a distribution policy at a child location level, according to an exemplary embodiment;

FIGS. 6A-6B are illustrations of content on a user interface showing steps performed by a user to add a child location to an existing distribution policy, according to an exemplary embodiment.

DETAILED DESCRIPTION

Figure 2A:
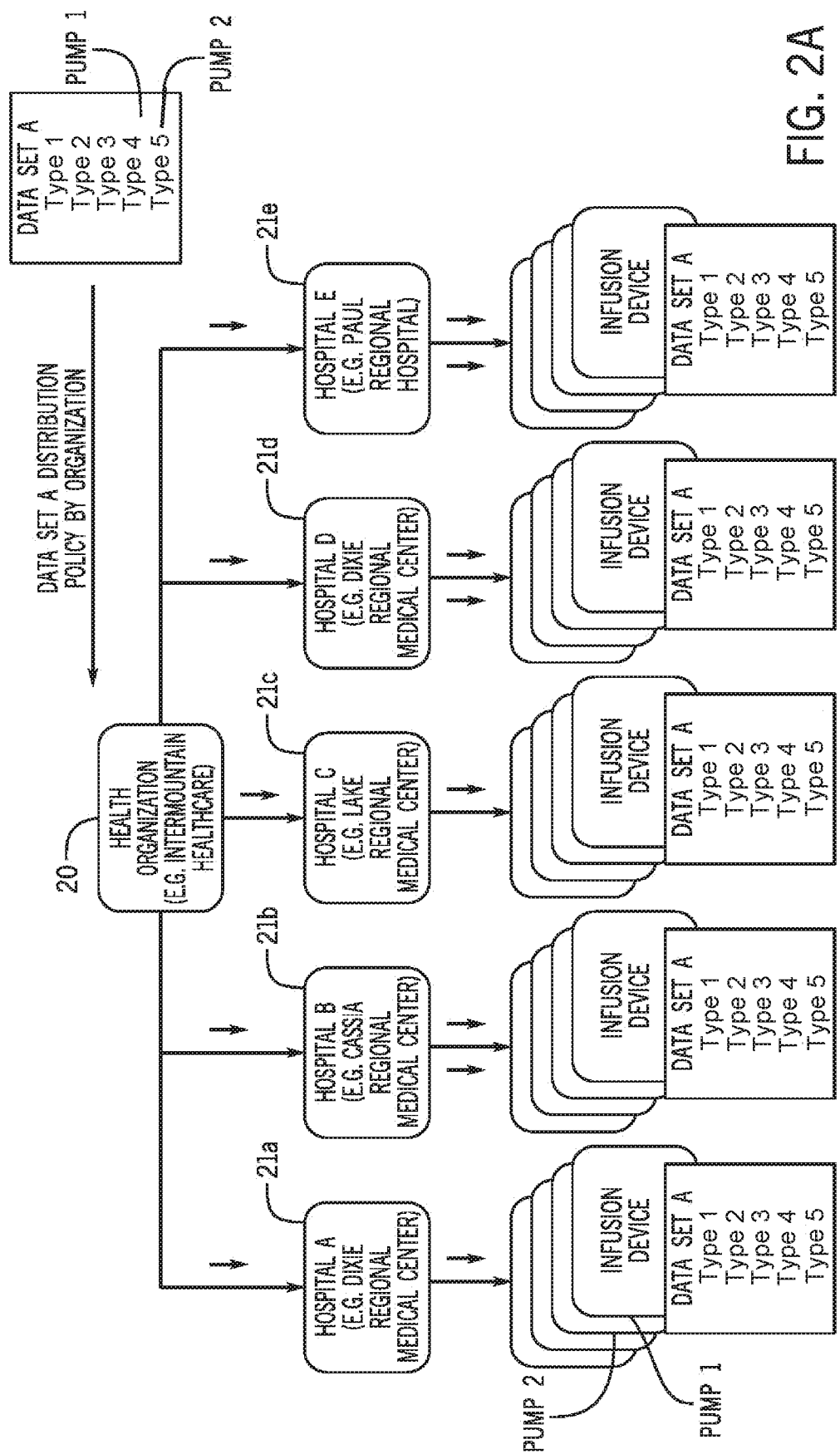
FIGS. 2A-2C are diagrammatic views showing data set distribution flow for a parent location and child location(s), according to several exemplary embodiments.

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

The following discloses example methods, apparatus, systems, and articles of manufacture including, among other components, firmware and/or software executed on hardware. It should be noted that such methods, apparatus, systems and articles of manufacture are illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

When any of the appended claims are read to cover a purely software and/or firmware implementation, at least one of the elements is hereby expressly defined to include a tangible medium such as a memory, a digital video disc (DVD), compact disc (CD), BLU-RAY™, etc. storing the software and/or firmware.

Some embodiments may enable healthcare facilities and/or hospitals to use default data set(s) for their medical devices rather than having to configure data sets each time for individual medical devices.

Some embodiments may facilitate management of medical devices including blood collection or apheresis devices, infusion pumps, drug delivery pumps, and/or other medical devices. For example, an infusion pump may infuse fluids, medication, or nutrients into a patient. An infusion pump may be used intravenously, subcutaneously, arterially, and/or epidurally, for example. For example, an infusion pump may administer injections at a variety of rates (e.g., injections too small for an intravenous (IV) drip (e.g., 0.1 mL per hour), injections per minute, injections with repeated boluses, patient-controlled injections up to maximum number per hour, or injections of fluids whose volumes vary by time of day, etc.).

In certain examples, an operator (e.g., a technician, nurse, etc.) may provide input regarding type of infusion, mode, and/or other device parameter. For example, continuous infusion may provide small pulses of infusion (e.g., between 500 nanoliters and 10 milliliters), with a pulse rate based on a programmed infusion speed. Intermittent infusion may alternate between a high infusion rate and a low infusion rate with timing programmable to keep a cannula open, for example. Patient-controlled infusion may provide on-demand infusion with a preprogrammed ceiling to avoid patient intoxication. The infusion rate may be controlled by a pressure pad or button that can be activated by the patient, for example. Infusion pumps may include large volume pumps (e.g., for nutrient solution delivery to feed a patient), small-volume pumps (e.g., for medicine delivery), etc.

In some embodiments, an operator or administrator may configure a medical device, such as an infusion pump, apheresis device, etc., and/or set one or more parameters for interaction between the device and a domain controller and/or a provider data management system. Certain examples may provide flexibility in facilitating operator and/or administrator (e.g., user) operation and configuration of a medical device while maintaining device reliability and security through new authorization protocols and systems.

Some embodiments may facilitate distribution of a data set to a medical device, such as an infusion pump, apheresis device, etc., while the medical device is in operation (e.g., during infusion of a patient via the infusion pump, etc.). Certain examples may determine and/or update a data set distribution policy associated with a medical device data management system. If a data set distribution policy has been created, then a new or updated data set (e.g., derived from a new or updated drug library) may be distributed to one or more medical devices, even if one or more of the target medical devices are currently operating (e.g., pump(s) are currently infusing drug into a patient) and/or even if a pre-existing data set is associated with the target medical device(s).

A data management system may interact with medical devices for flexible, remote configuration and operation while helping to ensure data and configuration safety and security, for example. An example of a data management system is described in greater detail in U.S. Patent Publication No. 2010/0049542, the contents of which are incorporated by reference herein in its entirety. Medical device operation and data set distribution may be performed simultaneously.

In certain examples, a data set may define an instruction set and/or drug settings for a medical device such as a "smart" infusion pump, apheresis device, etc. For example, "smart" infusion pumps may utilize a drug library and/or dose error reduction software to perform functions that assist healthcare providers with programming and calculating drug dose and delivery rates. The drug library may be a database and/or software that stores drug dosing information, including dosing limits, concentration, infusion parameters, and drug specific advisories, for example. A drug library may generate instructions to create a suitable data set and may help reduce or prevent medication errors and associated patient harm, for example. A data set generated by a drug library may be distributed to medical devices by downloading directly at the medical device or remotely over a network, e.g., from a data management system to multiple medical devices, etc.

In some examples, drug libraries may let clinicians select medications and fluids from preloaded lists, which can be tailored to a healthcare facility, patient care area, etc. For example, a drug library profile used in an intensive care unit (ICU) may include vasoactive medications, but a drug library for a surgical unit may not include such medication. Some facilities may also integrate smart infusion devices with electronic medical records, computerized order entry systems, and/or medication barcode scanning systems. Integrating these systems with smart pumps may provide additional safety checks that may make administering medications safer. Healthcare facilities may choose to implement limitations, commonly called hard and soft limits (also referred to as dosing limits), on preselected drugs via the drug library. The limits set lower and upper bounds on dosage, infusion rate, etc., as defined by hospital, health system, clinic, etc. Infusion pumps and/or other devices may generate usage reports regarding how the pumps have been used, which drugs have been administered (e.g., type, frequency, dosage, total quantity, etc.), dose overrides, etc.

Turning to FIG. 1, an example medical device management system 100 is shown. A data management system 110 may retrieve and/or generate instructions from a data library 120 (e.g., drug library) to form a data set 125. The data management system 110 may distribute the data set 125 to one or more target medical devices 130, 135 (e.g., pump(s), apheresis device(s), etc.) according to a specified distribution policy. The data set distribution may occur when a target medical device 130, 135 detects that the target data set 125 is different from its current data set. The data management system 110 may include a user interface 140 that provides for an authorized user to control and/or revise the data set 125. An authorized user may also control and/or revise the distribution policy governing distribution of the data set 125 via the user interface 140.

An organization may have a specified data set distribution policy to govern what data sets are distributed and the various ways data sets are distributed. A specific data set may be distributed to multiple medical devices in an organization. A data set may also be distributed to a specific location (e.g, hospital, building, ward, room) and/or to specific types of medical devices (e.g, infusion pumps, apheresis devices, etc.). The distribution policy may also call for a default data set to be automatically associated with any newly added medical devices, according to the existing data set policy for its location. An example of data set distribution is described in greater detail in U.S. Patent Application No. 62/259,942, the contents of which are incorporated by reference herein in its entirety.

FIG. 2A depicts an example of a distribution policy providing that when a data set is created for a parent location, e.g., organization, the data set is automatically inherited by each child location, e.g., hospital. Data Set A in the example in FIG. 2A may have been created for a health organization 20 by a data management system and a data/drug library. Data Set A may be configured to propagate to each child hospital 21a-21e per the distribution policy of the health organization 20 for Data Set A. Within each child hospital 21a-21e, Data Set A may be distributed into every medical device specified by Data Set A that is located within the child hospital. For example, if Data Set A specifies settings for Pump 1 and Pump 2, and child hospital 21a employs both Pumps 1 and Pumps 2, Data Set A may be distributed into every Pump 1 and every Pump 2 within child hospital 21a. Upon an authorized user's confirmation of the aforementioned distribution scheme for Data Set A, a data management system may automatically update all Pumps 1 and all Pumps 2 with the new data within Data Set A. The distribution of Data Set A to target devices may commence immediately after the data set policy is created or be programmed to commence at a later time. When a new pump is added later to a child hospital after distribution of Data Set A has completed, and the pump is a type that is specified by Data Set A, the new pump may automatically download Data Set A according to the existing data set policy for health organization 20.

Figure 2B:
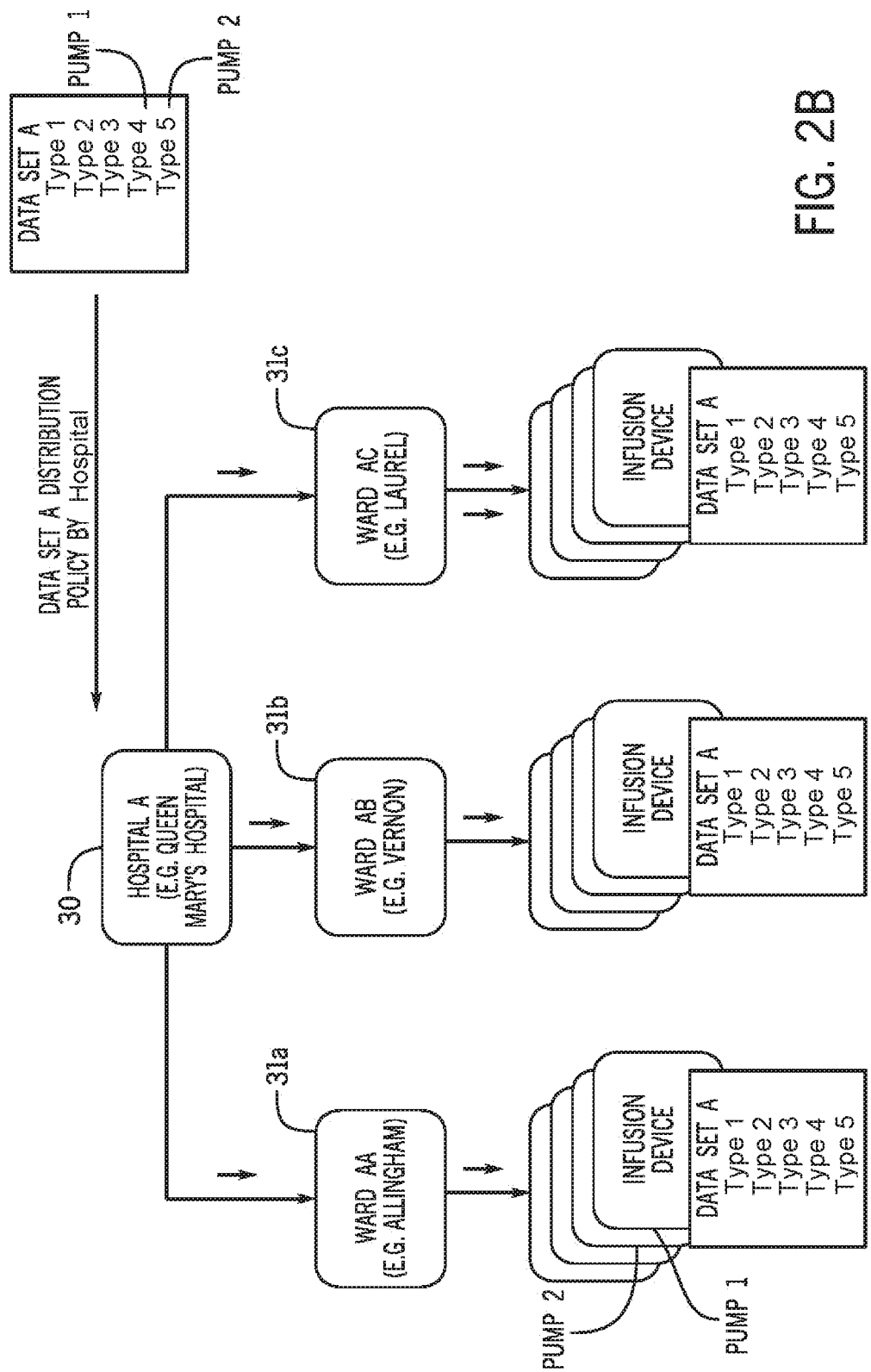

FIG. 2B illustrates an example of a data set inheritance policy in which the parent location is a hospital and the child location is a ward. Data Set A may be created for a parent hospital 30 by a data management system and a data/drug library. Data Set A may be configured to propagate to each ward 31a-31c per the distribution policy set for the parent hospital 30 for Data Set A. Within each ward, 31a-31c, Data Set A may be distributed into every medical device specified by Data Set A that is located within the ward. For example, if Data Set A specifies settings for Pump 1 and Pump 2, and ward 31a employs both Pumps 1 and Pumps 2, Data Set A may be distributed into every Pump 1 and every Pump 2 within ward 31a. Upon an authorized user's confirmation of the distribution scheme for Data Set A, a data management system may automatically update all Pumps 1 and all Pumps 2 with the new data within Data Set A. The distribution of Data Set A to target devices may commence immediately after the data set policy is created or be programmed to commence at a later time. When a new pump is added later to a ward after distribution of Data Set A has completed, and the pump is a type that is specified by Data Set A, the new pump may automatically download Data Set A according to the existing data set policy for parent hospital 30.

Figure 2C:
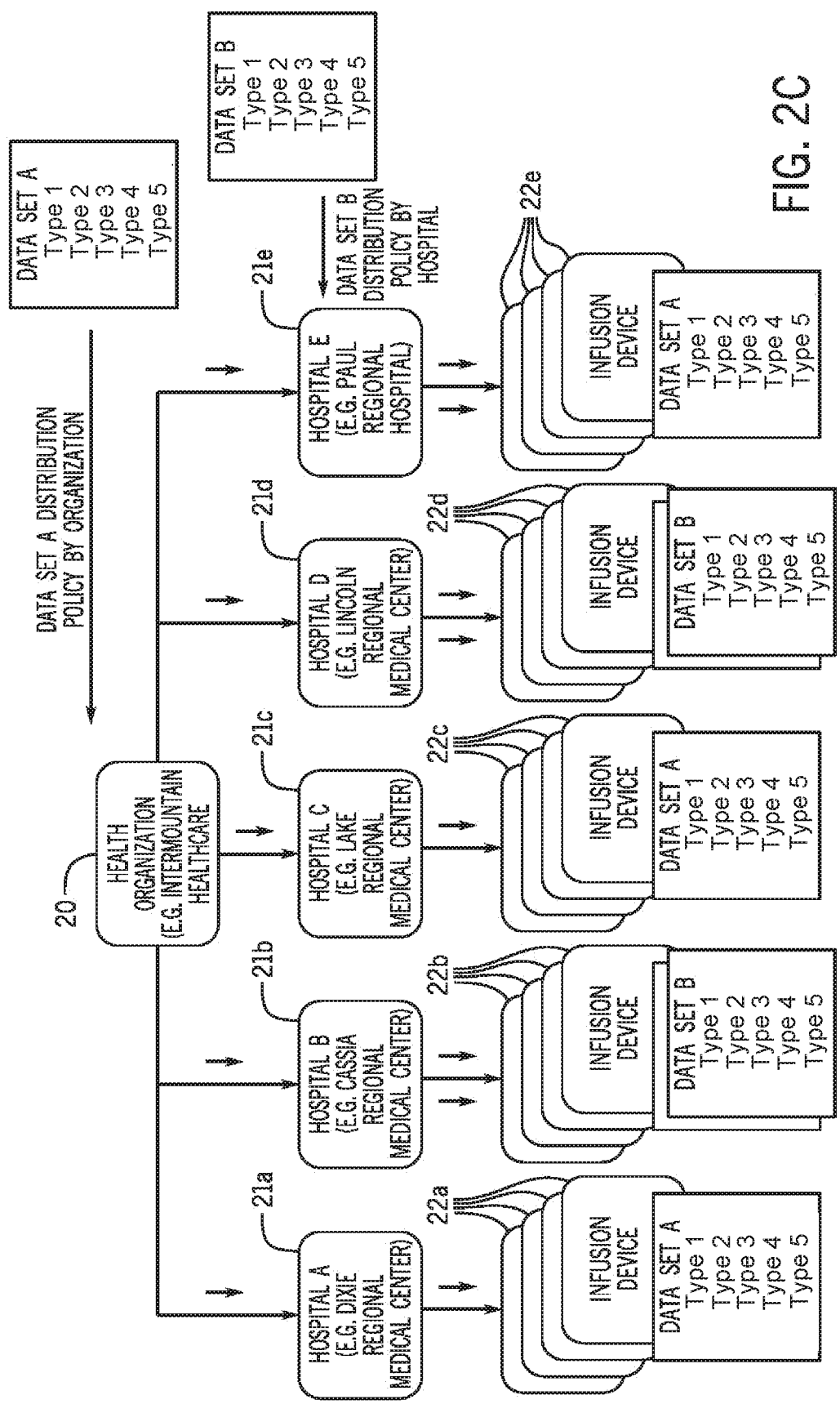

FIG. 2C illustrates an example of a selective inheritance policy for different data sets in which the parent location has one data set policy and select child locations have another data set policy. Data Set A in the example in FIG. 2C may have been created for a health organization 20 by a data management system and a data/drug library. Data Set A may be configured to propagate to each child hospital or ward 21a-21e per the distribution policy of the health organization 20 for Data Set A. Within each child hospital or ward 21a-21e, Data Set A may be distributed into every medical device specified by Data Set A that is located within the child hospital or ward. One or more child location 21b, 21d may require having its own location-specific Data Set B that is different from Data Set A and may need the new Data Set B to be distributed to all target devices in its location. An authorized user may build or select a data set and a distribution policy for that data set to be distributed location-specifically.

The distribution of a new Data Set B to select child locations 21b, 21d to which the previous Data Set A has already been distributed may be accomplished by overwriting Data Set A only in the specific child locations 21b, 21d. The distribution of Data Set B to target child locations 21b, 21d may also commence prior to completion of distribution of Data Set A to all child locations 21a-21e. In such an event, a data management system may first stop distribution of Data Set A for all target medical devices that have not yet received it and that have been specified as target devices 22b, 22d for new Data Set B. The target medical devices 22b, 22d may then be put on notice by the data management system regarding the identity of a new incoming data set policy and will require their new data set policy to be based on Data Set B. Distribution of Data Set B to target medical devices 22b, 22d may then commence. It can be seen from FIG. 2C that the target devices 22b, 22d impacted by the new policy initiated at the child location level will receive the new Data Set B but the other devices 22a, 22c, 22e in respective child locations 21a, 21c, 21e in the umbrella of parent organization 20 will still have Data Set A as distributed previously. Data set policies may thus be applied in a first-in-first-out (FIFO) order based on the time the policy was created. For example, in a FIFO situation where Data Set B and its distribution policy are created later in time than Data Set A and its distribution policy, then medical devices 22b, 22d that are target devices for both Data Set A and Data Set B will adopt the later created data set, i.e., Data Set B.

EXAMPLES

The following are examples of steps an authorized user may perform to set up, create, edit, and/or distribute a data set and/or distribution policy for a health organization and its child locations, using a user interface, such as the interface 140 depicted in FIG. 1, according to various exemplary embodiments. The user interface may comprise a monitor, keyboard, mouse, touch screen, voice/speech platform, and/or any suitable interface, that is in communication with a data management system, such as the system 110 depicted in FIG. 1.

Figure 3:
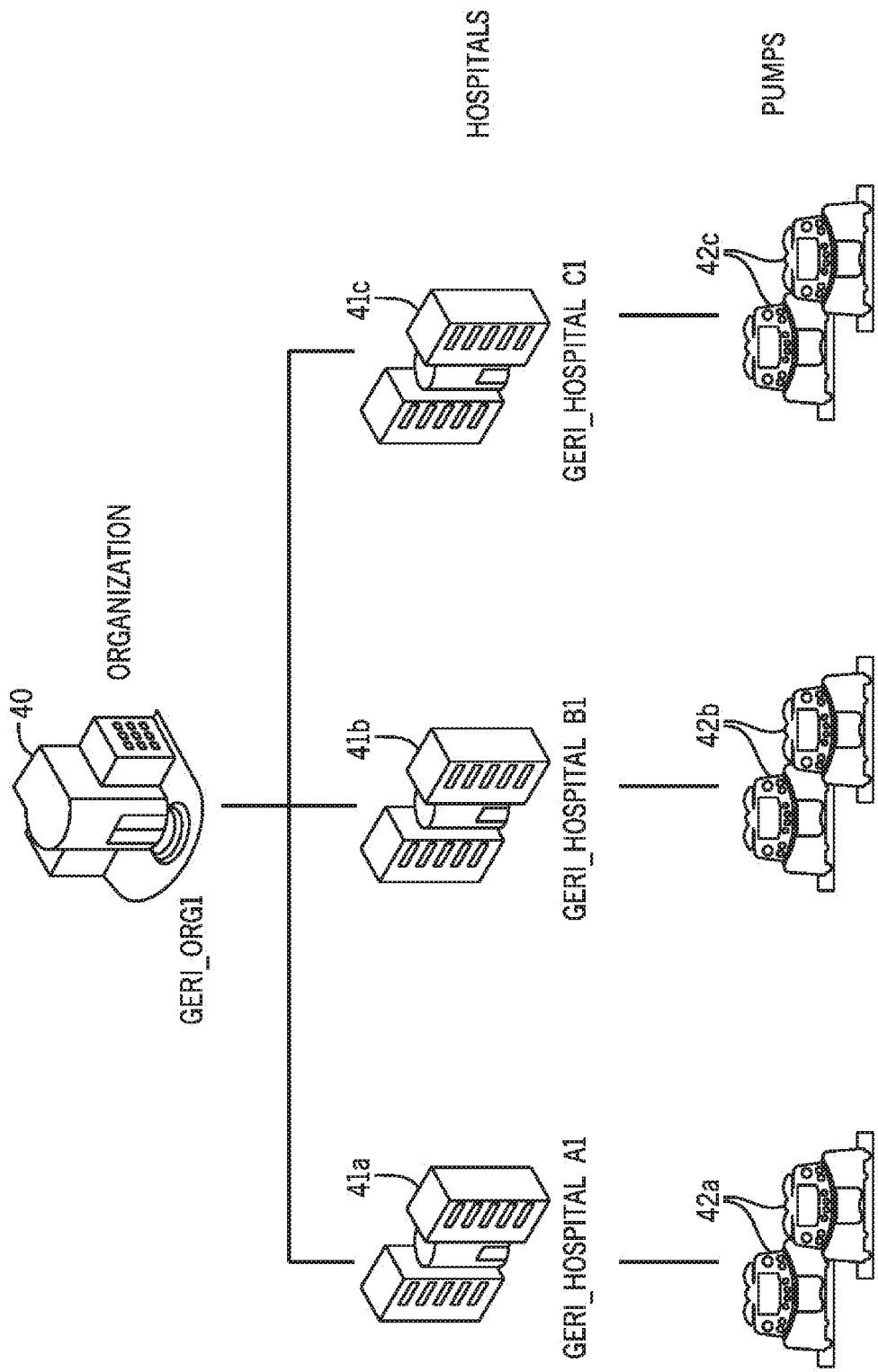
FIG. 3 is a schematic view of an organizational structure of a health organization, including child hospitals and child hospital medical devices, according to an exemplary embodiment.

FIG. 3 illustrates an example organizational structure of a health organization 40 and its child hospitals 41a-41c and each child hospital's pumps 42a-42c for which an authorized user may set up, create, edit, and/or distribute a data set and/or distribution policy.

Figure 4B:
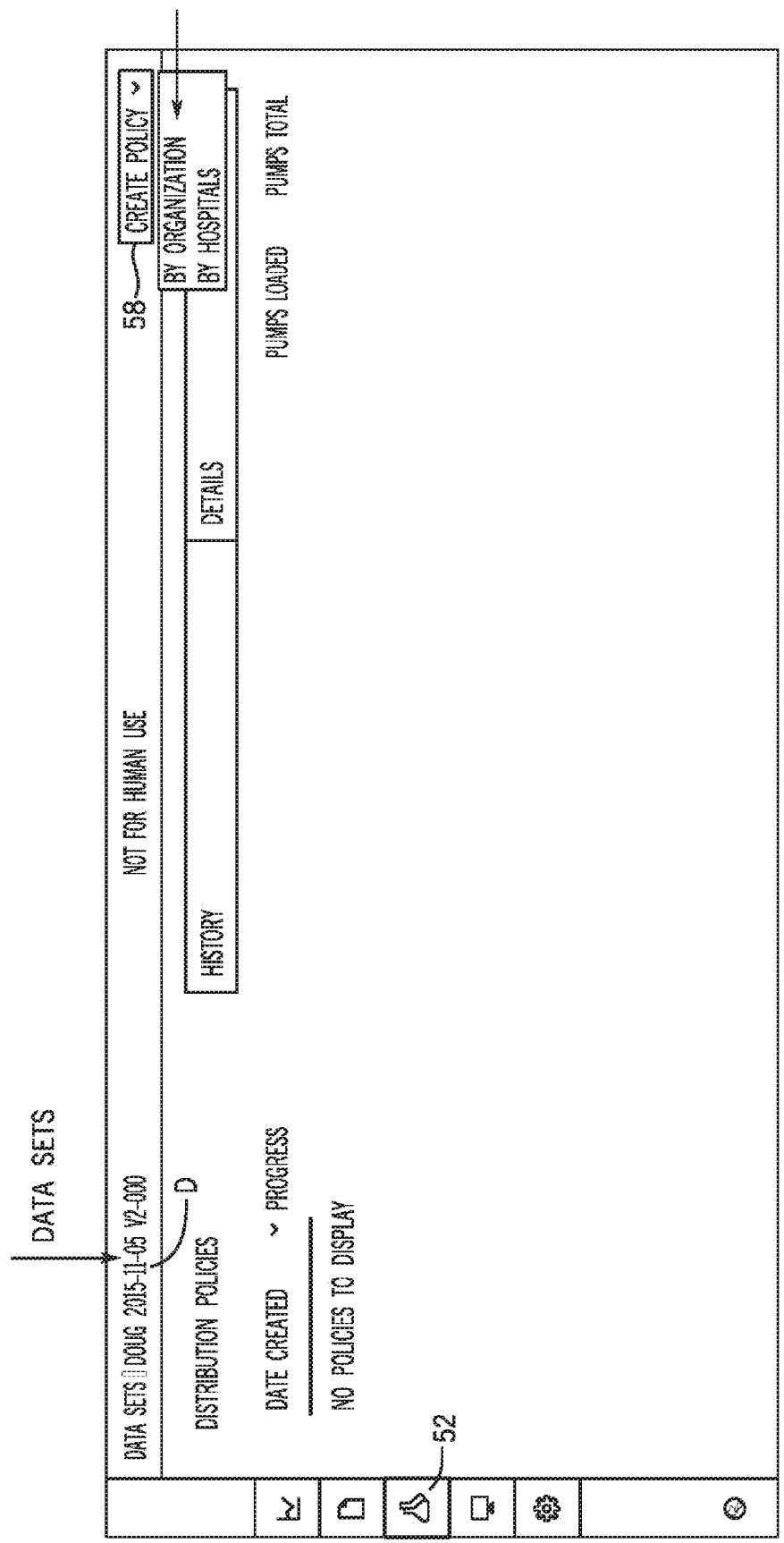
Figure 4C:
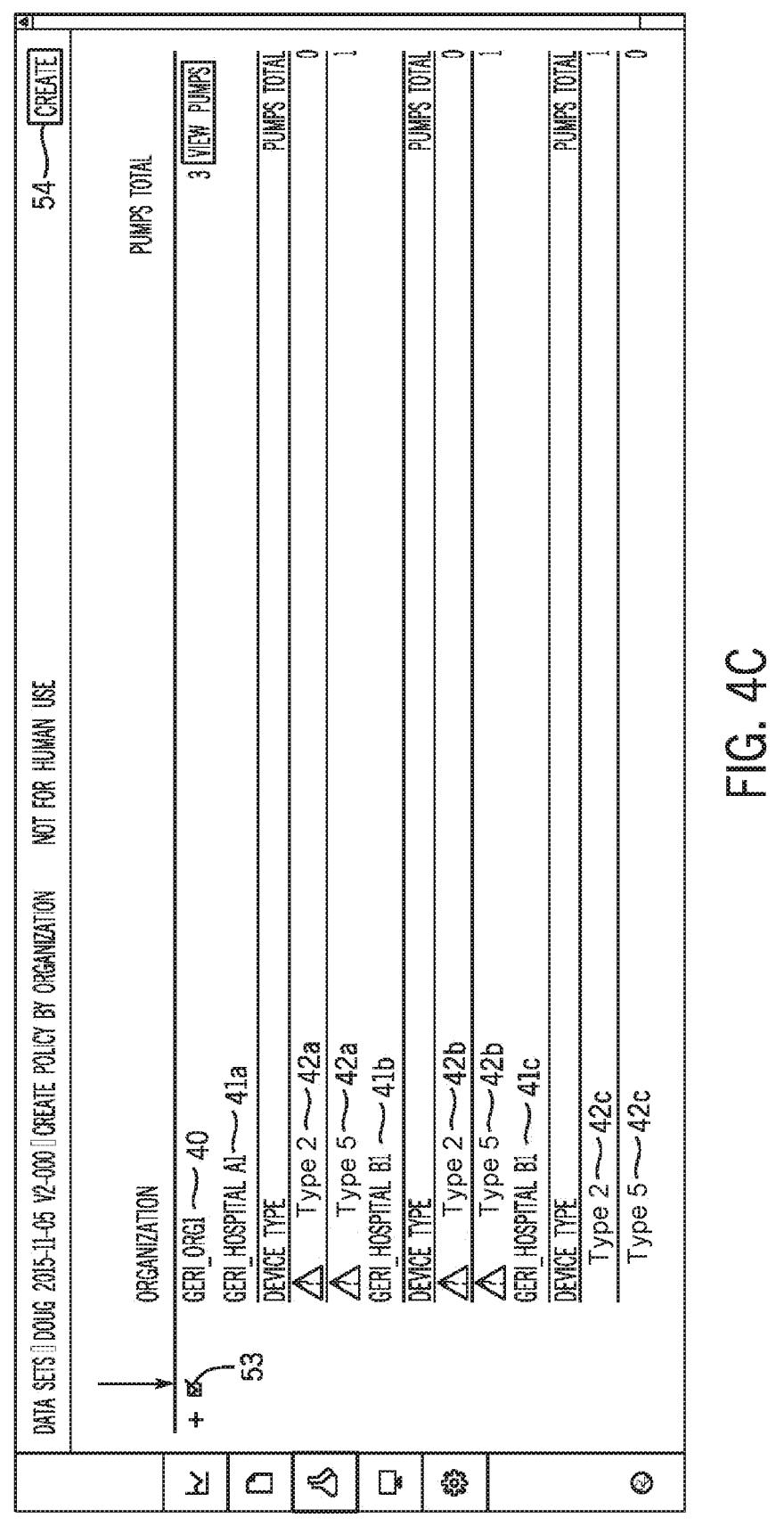
Figure 4D:
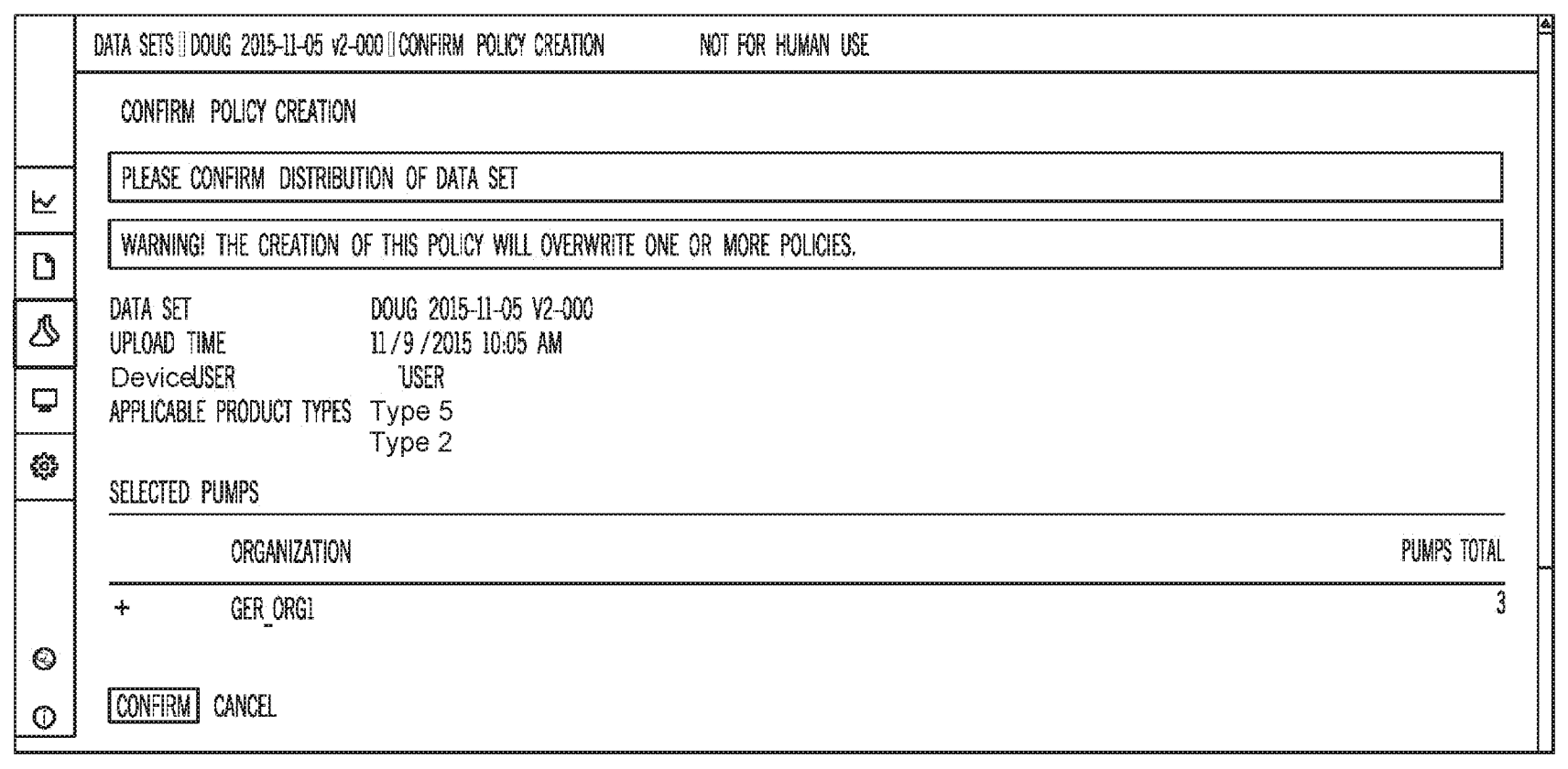
Figure 4E:
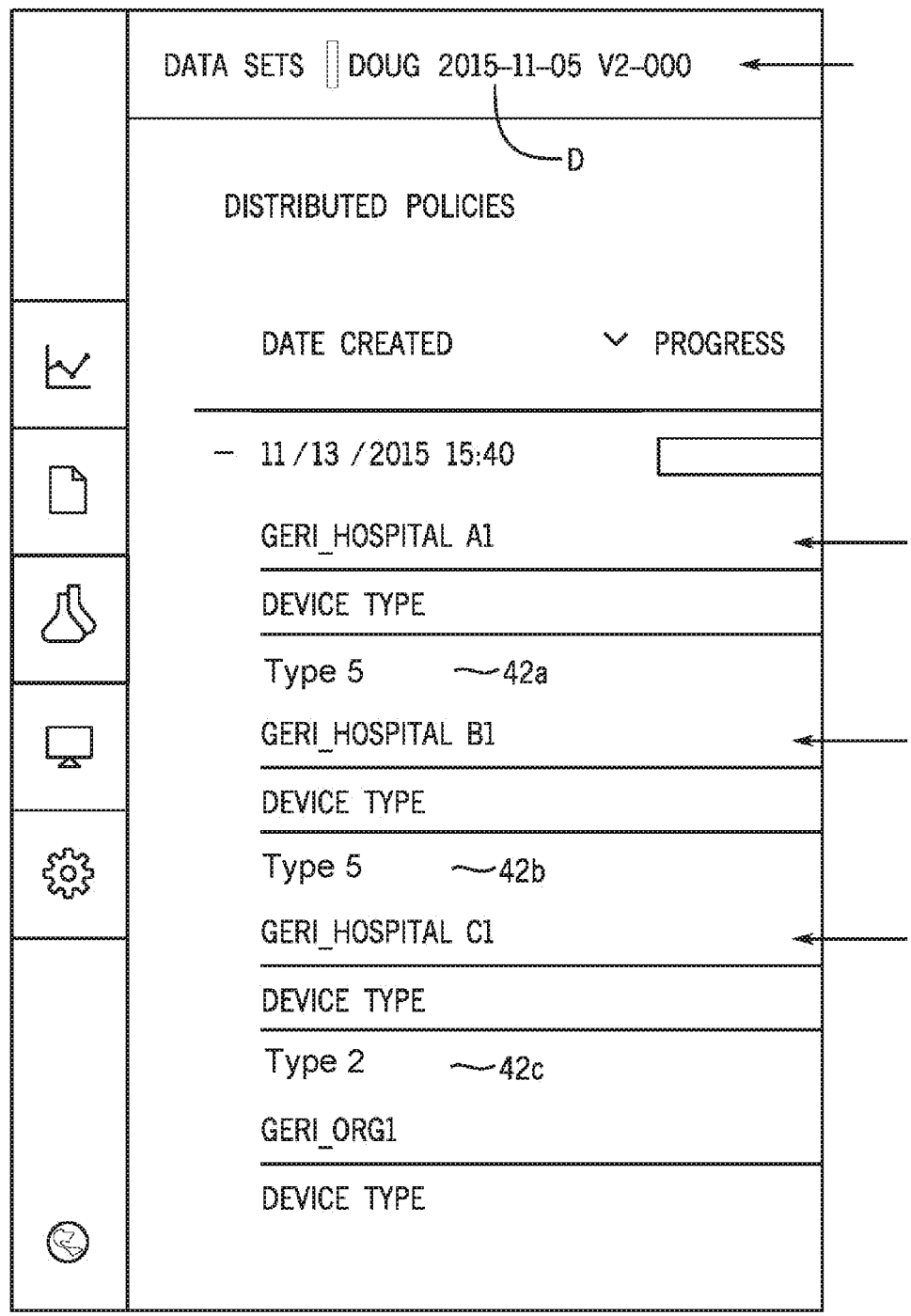

In an embodiment in which the user interface is a monitor or touch screen, FIG. 4A depicts content displayed on the screen that an authorized user may see within a configuration tab 51 on the screen. FIG. 4A shows that all child hospitals 41a-41c under health organization 40 are recognized and configured in the data management system. FIG. 4B depicts content displayed within a data sets tab 52. Data Set D is shown to be an available data set for the health organization 40. A distribution policy for Data Set D may be configured at the organizational level by selecting "By Organization" from a "Create Policy" drop down menu 58 on the screen. The next screen depicted by FIG. 4C lists health organization 40 and all of its child hospitals 41a-41c and each child hospital's pumps 42a-42c. To distribute Data Set D to all of organization 40, the authorized user may check the check box 53 next to health organization 40 and click the "Create" button 54 to create the distribution policy for Data Set D. The user may then confirm on the next screen shown in FIG. 4D the distribution of Data Set D. The next screen shown in FIG. 4E shows that all medical devices 42a-42c specified by Data Set D in organization 40 will receive Data Set D.

Figure 5A:
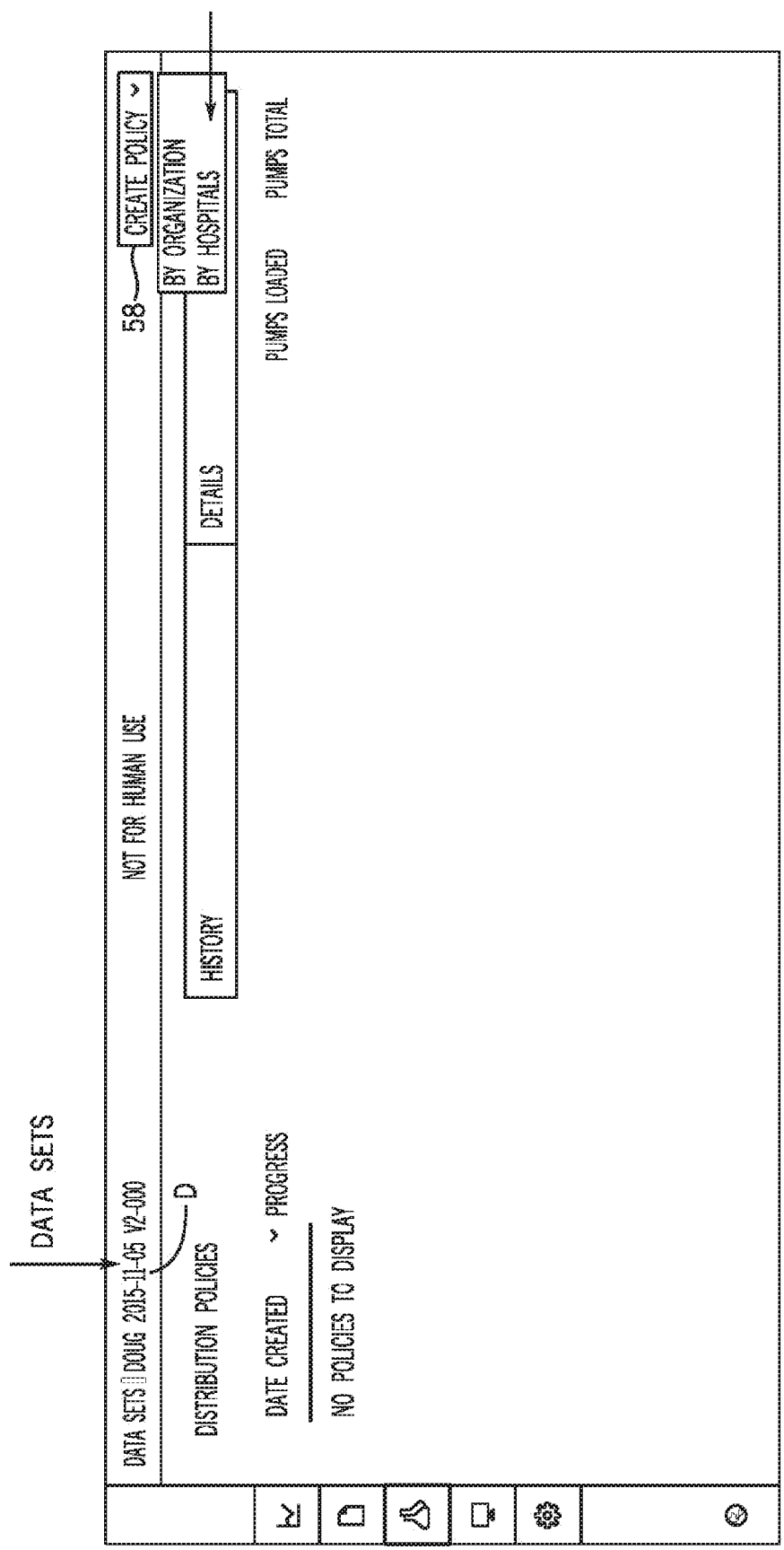
Figure 5C:
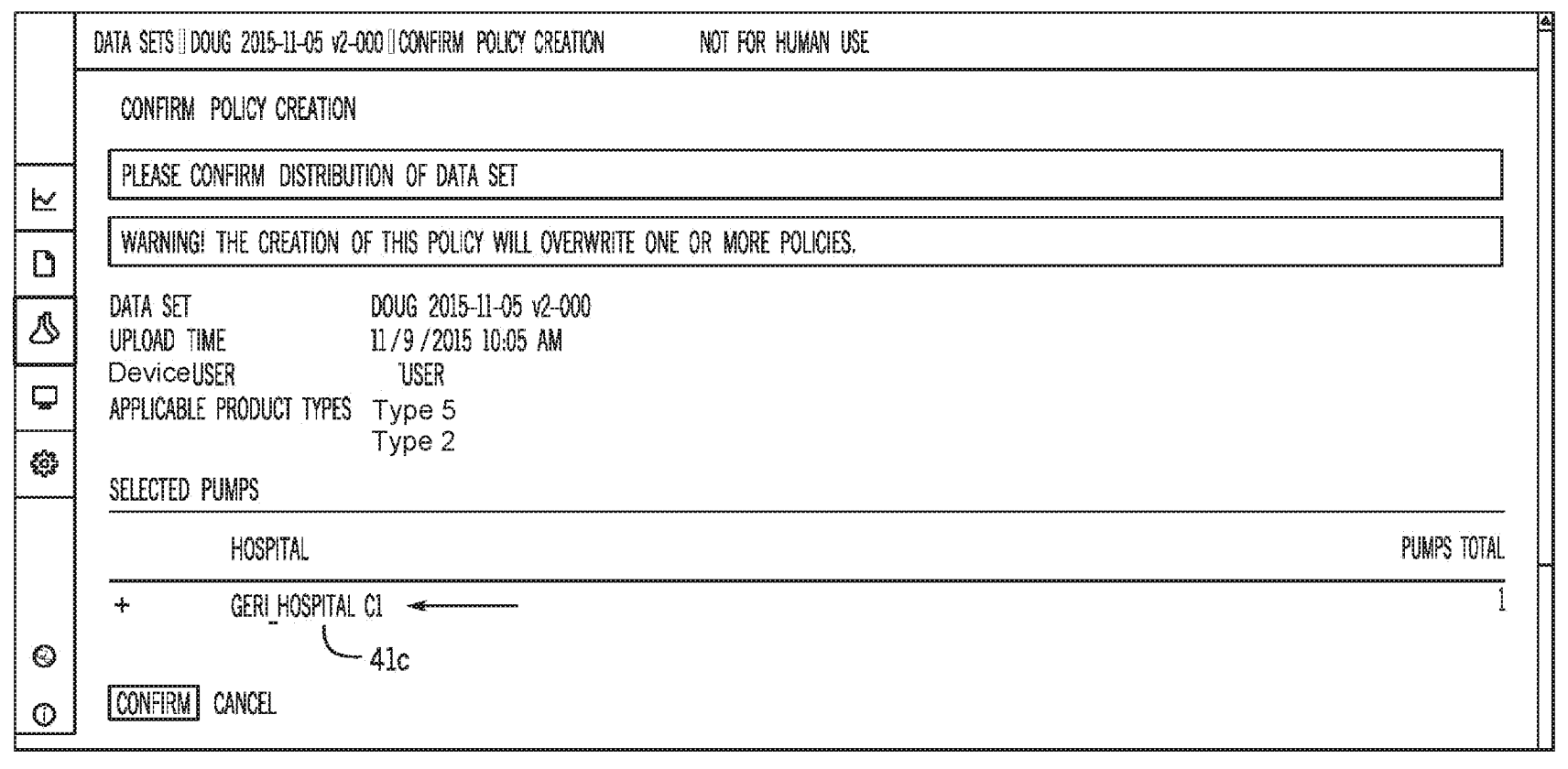
Figure 5D:
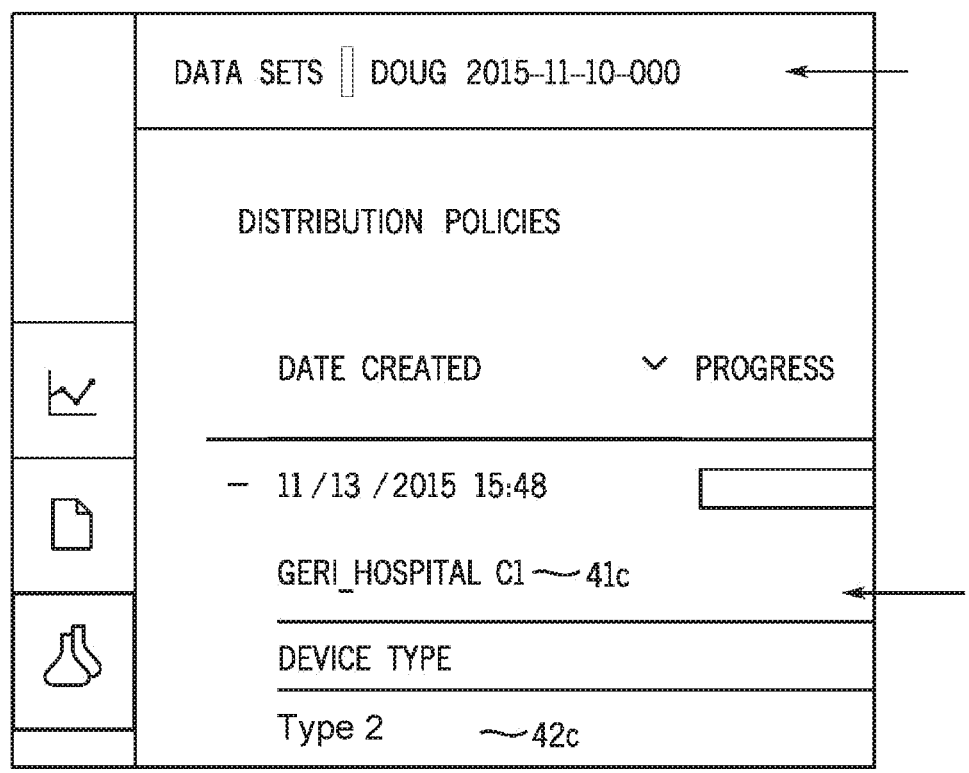

A distribution policy for a specific data set may also be configured by an authorized user at the child location level by navigating to the screen depicted in FIG. 4B. A distribution policy for Data Set D may be configured at the child location level by selecting "By Hospitals" from the "Create Policy" drop down menu 58 on the screen shown in FIG. 5A. The next screen depicted by FIG. 5B lists all of the child hospitals 41a-41c under health organization 40. To distribute Data Set D to select child locations, for example, child location 41c, the authorized user may check the check box 55 next to child location 41c and click the "Create" button 56 to create the distribution policy for Data Set D. The user may then confirm on the next screen shown in FIG. 5C the distribution of Data Set D for child location 41c. The next screen shown in FIG. 5D shows that all medical devices 42c specified by Data Set D within child location 41c will receive Data Set D.

Figure 6B:
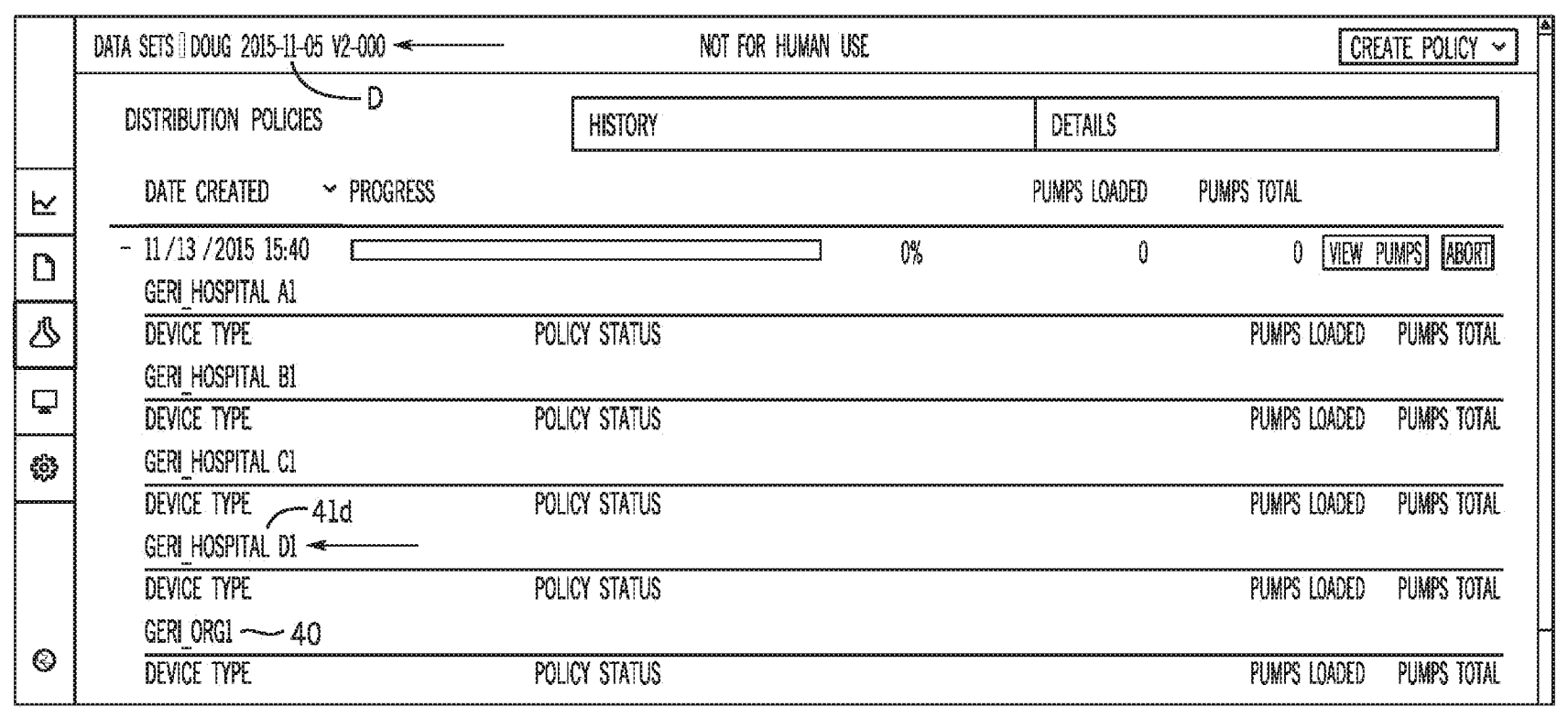

After a data set policy is set for an organization, such as previously shown in FIGS. 4A-4E, a new child location for the organization may be configured, and the new child location may automatically inherit the default data set for the organization. An authorized user may return to the configurations tab 51 shown in FIG. 4A. The "Create Hospital" button 57 may be used to add a new child location and its associated medical devices. FIG. 6A shows child hospital 41d having been added to the health organization. Selecting the data sets tab 52, the user can see in the screen shown in FIG. 6B that Data Set D, which is the default data set for organization 40, has been inherited by child location 41d, according to the existing data set distribution policy for organization 40.

Figure 7:
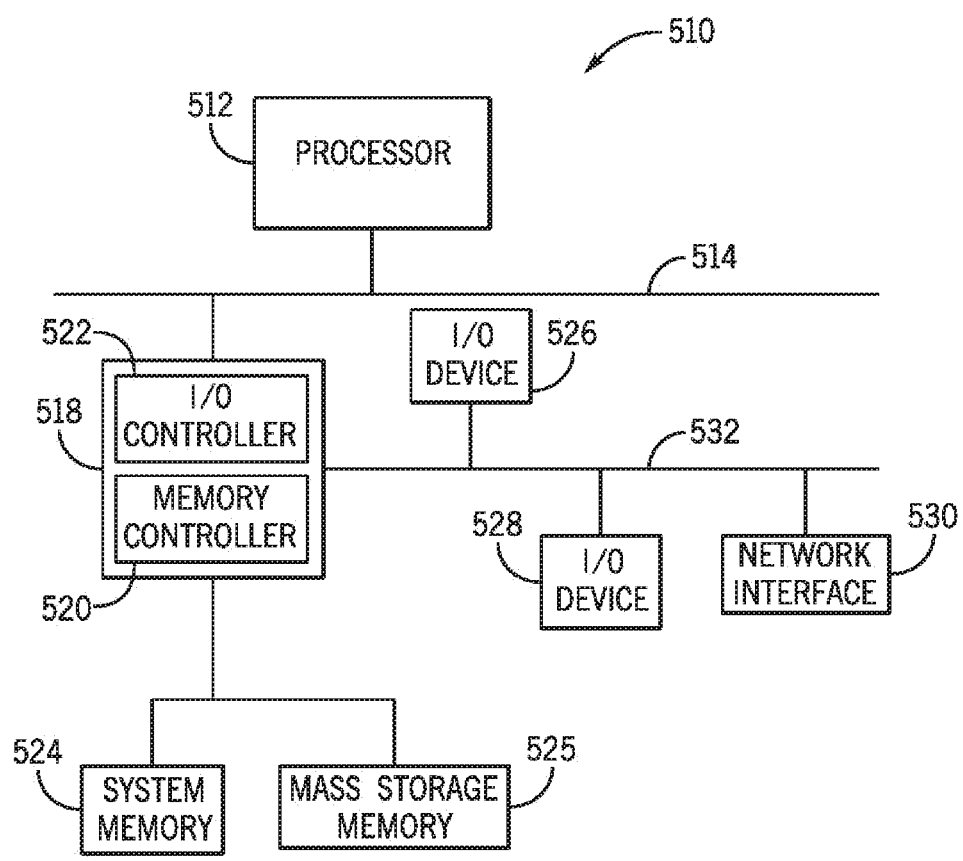
FIG. 7 is a block diagram of a data management system/server computer for processing medical device data for presentation on a user interface, according to an exemplary embodiment.

FIG. 7 is a block diagram of a data management system and/or server computer for processing medical device data for presentation on a display, according to an illustrative embodiment. In alternate embodiments, the systems and methods described herein may be implemented on a single server computer, a plurality of server computers, a server farm, a cloud server environment, or using other computer resources. Data management system/server 110 and medical devices 130, 135 may comprise analog and/or digital circuit components forming processing circuits configured to perform the steps described herein. The processing circuits may comprise discrete circuit elements and/or programmed integrated circuits, such as one or more microprocessors, microcontrollers, analog-to-digital converters, application-specific integrated circuits (ASICs), programmable logic, printed circuit boards, and/or other circuit components. Data management system/server 110 and medical devices 130, 135 may each comprise a network interface circuit configured to provide communications over one or more networks with each other and/or with other device. The network interface circuit may comprise digital and/or analog circuit components configured to perform network communications functions. The networks may comprise one or more of a wide variety of networks, such as wired or wireless networks, wide area-local-area or personal-area networks, proprietary or standards-based networks, etc. The networks may comprise networks such as an Ethernet network, networks operated according to Bluetooth protocols, IEEE 802.11x protocols, cellular (TDMA, CDMA, GSM) networks, or other network protocols. The network interface circuits may be configured for communication of one or more of these networks and may be implemented in one or more different sub-circuits, such as network communication cards, internal or external communication modules, etc.

According to one embodiment, storage of the infusion data records may be implemented on a database coupled to or part of data management system/server 110. The database may be a DBMS hosted on a server host platform, such as Microsoft Windows XP, Microsoft Windows Server 2008, etc.

Referring again to FIG. 7, a block diagram of an example processor system 510 is shown that can be used to implement systems, articles of manufacture, and methods described herein. As shown in FIG. 7, the processor system 510 includes a processor 512 that is coupled to an interconnection bus 514. The processor 512 can be any suitable processor, processing unit, or microprocessor, for example. Although not shown in FIG. 7, the system 510 can be a multiprocessor system and, thus, can include one or more additional processors that are identical or similar to the processor 512 and that are communicatively coupled to the interconnection bus 514.

The processor 512 of FIG. 7 is coupled to a chipset 518, which includes a memory controller 520 and an input/output ("I/O") controller 522. A chipset may provide I/O and memory management functions as well as a plurality of general purpose and/or special purpose registers, timers, etc. that are accessible or used by one or more processors coupled to the chipset 518. The memory controller 520 performs functions that enable the processor circuit 512 (or processors if there are multiple processors) to access a system memory 524 and a mass storage memory 525.

The system memory 524 can include any desired type of volatile and/or non-volatile memory such as, for example, static random access memory (SRAM), dynamic random access memory (DRAM), flash memory, read-only memory (ROM), etc. The mass storage memory 525 can include any desired type of mass storage device including hard disk drives, optical drives, tape storage devices, etc.

The I/O controller 522 performs functions that enable the processor 512 to communicate with peripheral input/output ("I/O") devices 526 and 528 and a network interface 530 via an I/O bus 532. The I/O devices 526 and 528 can be any desired type of I/O device such as, for example, a keyboard, a video display or monitor, a mouse, etc. The network interface 530 can be, for example, an Ethernet device, an asynchronous transfer mode device, an 802.11 device, a DSL modem, a cable modem, a cellular modem, etc. that enables the processor system 510 to communicate with another processor system.

While the memory controller 520 and the I/O controller 522 are depicted in FIG. 7 as separate blocks within the chipset 518, the functions performed by these blocks can be integrated within a single semiconductor circuit or can be implemented using two or more separate integrated circuits.

Certain embodiments contemplate methods, systems and computer program products on any machine-readable media to implement functionality described above. Certain embodiments can be implemented using an existing computer processor, or by a special purpose computer processor incorporated for this or another purpose or by a hardwired and/or firmware system, for example.

Some or all of the system, apparatus, and/or article of manufacture components described above, or parts thereof, can be implemented using instructions, code, and/or other software and/or firmware, etc. stored on a tangible machine accessible or readable medium and executable by, for example, a processor system (e.g., the example processor system 510 of FIG. 7). Tangible computer readable media include a memory, DVD, CD, etc. storing the software and/or firmware, but do not include a propagating signal.

As used herein, the term tangible computer readable medium includes any type of computer readable storage and excludes propagating signals. Additionally or alternatively, the example processes described herein may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information).

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. A computer-implemented medical device management method for distributing data sets to a plurality of medical devices in child locations of a parent health organization, the child locations being hospitals or wards, said method comprising:
   providing a first data set that has been created for the parent health organization by both a data management system and a drug library;
   receiving a first user input via a user interface to distribute the first data set to the parent health organization;
   distributing the first data set to the medical devices specified by the first data set located in the child locations within the parent health organization per distribution policy of the parent health organization for the first data set;
   facilitating operation of medical devices according to the first data set;
   providing a second location specific data set that is different from the first data set and that is to be distributed to medical devices in select child locations;
   receiving a second user input to distribute the second data set to the select child locations, wherein the second user input is received after the first user input;
   commencing distribution of the second data set to the select child locations prior to completion of distributions of the first data set to all child locations, and
   upon commencing distribution of the second data set, stopping distribution of the first data set for all target medical devices that have not yet received the first data set and that have been specified as target devices for the second data set in the select child locations, such that the target medical devices in the select child locations receive the second data set but other medical devices in the select child locations still have the first data set as distributed previously, with distribution of the first data set continuing to the medical devices specified as target devices by the first data set and not by the second data set which have not yet received the first data set.

2. The method of claim 1, further comprising:
   receiving a user input to add a new medical device at at least one child location, wherein the new medical device is a type identified by the first data set;
   automatically distributing the first data set to the new medical device located at the at least one child location and facilitating operation of the new medical device according to the first data set.

3. The method of claim 1, further comprising:
   receiving a user input to add a new medical device at at least one child location, wherein the new medical device is a type identified by both the first and second data sets;
   distributing the second data set to the new medical device located at the at least one child location and facilitating operation of the new medical device according to the second data set.

4. The method of claim 1, wherein the medical device further comprises at least one of a blood collection device, an apheresis device, an infusion pump, and a drug delivery pump.

5. The method of claim 1, wherein the drug library further comprises a database and/or software that stores at least one of drug dosing information, dosing limits, concentration, infusion parameters, and drug specific advisories.

6. The method of claim 1, wherein the child locations are accessible through a wide-area network.

7. The method of claim 1, wherein the first data set and/or the second data set is distributed to a least one of said medical devices while said at least one of said medical devices is in operation.

8. A server computer configured to distribute data sets to a plurality of medical devices in child locations of a parent health organization, the child locations being hospitals or wards, the server computer comprising:
 a network interface circuit configured to provide communications over a network; and
 a processing circuit configured to:
  provide a first data set that has been created for the parent health organization by both a data management system and a drug library;
  receive a first user input via a user interface to distribute the first data set to the parent health organization;
  distribute the first data set to the medical device specified by the first data set located in the child locations within the parent health organization per distribution policy of the parent health organization for the first data set;
  facilitate operation of medical devices according to the first data set;
  provide a location specific second data set that is different from the first data set and that is to be distributed to medical devices in select child locations;
  receive a second user input to distribute the second data set to the select child locations, wherein the second user input is received after the first user input;
  commence distribution of the second data set to the select child locations prior to completion of distributions of the first data set to all child locations, and
  upon commencing distribution of the second data set, stop distribution of the first data set for all target medical devices that have not yet received the first data set and that have been specified as target devices for the second data set in the select child locations, such that the target medical devices in the select child locations receive the second data set but other medical devices in the select child locations still have the first data set as distributed previously, with distribution of the first data set continuing to the medical devices specified as target devices by the first data set and not by the second data set which have not yet received the first data set.

9. The server computer of claim 8, wherein the processing circuit is further configured to:
 add a new medical device at a child location, wherein the new medical device is a type identified by both the first and second data sets; and
 automatically distribute the second data set to the new medical device located at the child location and facilitate operation of the new medical device according to the second data set.

10. The server computer of claim 8, wherein the medical device further comprises at least one of a blood collection device, an apheresis device, an infusion pump, and a drug delivery pump.

11. The server computer of claim 8, wherein the drug library further comprises a database and/or software that stores at least one of drug dosing information, dosing limits, concentration, infusion parameters, and drug specific advisories.

12. The server computer of claim 8, wherein the child locations are accessible through a wide-area network.

13. The server computer of claim 8, wherein the first data set and/or the second data set is distributed to a least one of said medical devices while said at least one of said medical devices is in operation.

14. A computer-implemented medical device management system to distribute data sets to a plurality of medical devices in child locations of a parent health organization, the child locations being hospitals or wards, the system comprising:
 a data management system comprising analog and/or digital circuit components comprising discrete circuit elements and/or programmed integrated circuits;
 a medical device comprising a network interface circuit configured to provide communications over one or more networks with another medical device and/or with the data management system;
 wherein the data management system is configured to:
  provide a first data set that has been created for the parent health organization by both the data management system and a drug library;
  receive a first user input via a user interface to distribute the first data set to the parent health organization,
  distribute the first data set to the medical devices specified by the first data set located in the child locations within the parent health organization per distribution policy of the parent health organization for the first data set,
  facilitate operation of medical devices according to the first data set;
  provide a second location specific data set that is different from the first data set and that is to be distributed to medical devices in select child locations;
  receive a second user input to distribute the second data set to the select child locations, wherein the second user input is received after the first user input;
  commence distribution of the second data set to the select child locations prior to completion of distributions of the first data set to all child locations, and
  upon commencing distribution of the second data set, stop distribution of the first data set for all target medical devices that have not yet received the first data set and that have been specified as target devices for the second data set in the select child locations, such that the target medical devices in the select child locations receive the second data set but other medical devices in the select child locations still have the first data set as distributed previously, with distribution of the first data set continuing to the medical devices specified as target devices by the first data set and not by the second data set which have not yet received the first data set.

15. The computer-implemented medical device management system of claim 14, wherein the data management system, upon receiving user input to add a new medical device at a child location, is configured to automatically distribute the second data set to the new medical device and to facilitate operation of the new medical device according to the second data set.

16. The computer-implemented medical device management system of claim 14, wherein the medical device further comprises at least one of a blood collection device, an apheresis device, an infusion pump, and a drug delivery pump.

17. The computer-implemented medical device management system of claim 14, wherein the drug library further comprises a database and/or software that stores at least one of drug dosing information, dosing limits, concentration, infusion parameters, and drug specific advisories.

18. The computer-implemented medical device management system of claim 14, wherein the child locations are accessible through a wide-area network.

19. The computer-implemented medical device management system of claim 14, wherein the first data set and/or the second data set is distributed to a least one of said medical devices while said at least one of said medical devices is in operation.

* * * * *